(12) United States Patent
Barton et al.

(10) Patent No.: US 7,345,172 B2
(45) Date of Patent: Mar. 18, 2008

(54) METHODS AND COMPOSITIONS FOR DETECTING POLYNUCLEOTIDE DUPLEX DAMAGE AND ERRORS

(75) Inventors: Jacqueline K. Barton, San Marino, CA (US); Henrik Junicke, Luckenwalde (DE)

(73) Assignee: Calfornia Institute of Technology, Pasadena, CA (US)

( * ) Notice: Subject to any disclaimer, the term of this patent is extended or adjusted under 35 U.S.C. 154(b) by 454 days.

(21) Appl. No.: 10/974,474

(22) Filed: Oct. 26, 2004

(65) Prior Publication Data
US 2005/0148772 A1    Jul. 7, 2005

Related U.S. Application Data

(63) Continuation of application No. 10/015,997, filed on Dec. 10, 2001, now Pat. No. 6,808,884.

(60) Provisional application No. 60/254,497, filed on Dec. 8, 2000.

(51) Int. Cl.
C07D 242/36 (2006.01)
(52) U.S. Cl. .................... 544/342; 544/343
(58) Field of Classification Search .............. None
See application file for complete search history.

(56) References Cited

U.S. PATENT DOCUMENTS

| | | | |
|---|---|---|---|
| 5,157,032 A | 10/1992 | Barton | |
| 5,607,924 A | 3/1997 | Magda et al. | |
| 6,031,098 A | 2/2000 | Barton et al. | |
| 6,063,573 A | 5/2000 | Kayyem | |
| 6,071,699 A | 6/2000 | Meade et al. | |
| 6,087,100 A | 7/2000 | Meade et al. | |
| 6,090,933 A | 7/2000 | Kayyem | |
| 6,096,273 A | 8/2000 | Kayyem et al. | |
| 6,306,601 B1 | 10/2001 | Barton et al. | |
| 6,444,661 B1 | 9/2002 | Barton et al. | |
| 6,777,405 B2 * | 8/2004 | Barton et al. | ........... 514/185 |

FOREIGN PATENT DOCUMENTS

| | | |
|---|---|---|
| WO | WO 86/04358 | 7/1986 |
| WO | WO 99/09203 A1 | 2/1999 |

OTHER PUBLICATIONS

Danliker et al. Biochemistry 37:6491-6502 (1998).

(Continued)

*Primary Examiner*—Zachary C Tucker
(74) *Attorney, Agent, or Firm*—DLA Piper US LLP

(57) ABSTRACT

In accordance with the present invention there is provided a new class of sterically demanding metallo-intercalators. These compounds intercalate between bases in a duplex polynucleotide, but only where the bases are not fully complementary, for example, where there is a base-pair mismatch. The compounds are sufficiently sterically demanding that intercalation between bases in fully complementary duplexes does not occur to a significant degree. These mismatch intercalators are useful for detecting DNA and RNA defects, for diagnosing disorders characterized by the presence or increase in DNA and/or RNA defects, and for treating such disorders. Further, the compounds are capable of catalyzing photolytic cleavage of nucleic acids at relatively long wavelengths, and under normal sunlight.

25 Claims, 3 Drawing Sheets

OTHER PUBLICATIONS

The Stratagene Catalog p. 39 (1988).
Fletcher et al., "Structural, Electrochemical and UV/VIS/NIR Spectroelectrochemical Properties of Diastereomerically Pure Dinuclear Ruthenium Complexes Based on the Bridging Ligand Phenanthroline-5,6-Diimine, and a Mononuclear By-Product with a Peripheral Isoimidazole Group", *Journal of the Chemical Society, Dalton Transactions: Inorganic Chemistry*, (17), 2999-3006 (1999).
Jackson & Barton, "Recognition of DNA Base Mismatches by a Rhodium Intercalator", *Journal of the American Chemical Society*, 119:12986-12987 (1997).

* cited by examiner

Junicke.HJ100.2.Frac exp2    std1sh

| SAMPLE | | DEC. & VT | |
|---|---|---|---|
| date | Aug 27 2000 | dfrq | 300.080 |
| solvent | CDC13 | dn | H1 |
| file | exp | dpwr | 40 |
| ACQUISITION | | dof | 0 |
| sfrq | 300.082 | dm | nnn |
| tn | | dmm | c |
| at | 1.600 | dmf | 11600 |
| np | 32000 | PROCESSING | |
| sw | 10000.0 | lb | 1.00 |
| fb | 5600 | wtfile | |
| bs | 4 | proc | ft |
| ss | 4 | fn | 65536 |
| tpwr | 55 | | |
| pw | 15.4 | werr | |
| d1 | 1.000 | wexp | |
| tof | 1113.9 | wbs | |
| nt | 512 | wnt | |
| ct | 196 | | |
| alock | n | | |
| gain | 16 | | |
| FLAGS | | | |
| il | n | | |
| in | ny | | |
| dp | y | | |
| DISPLAY | | | |
| sp | 2221.1 | | |
| wp | 2412.5 | | |
| vs | 690 | | |
| sc | 0 | | |
| wc | 250 | | |
| hzmm | 9.65 | | |
| is | 41451.76 | | |
| rfl | 3757.5 | | |
| rfp | 0 | | |
| th | 37 | | |
| ins | 100.000 | | |
| nm | cdc   ph | | |

METHODS AND COMPOSITIONS FOR DETECTING POLYNUCLEOTIDE DUPLEX DAMAGE AND ERRORS

RELATED APPLICATIONS

This application is a continuation application of U.S. application Ser. No. 10/015,997 filed Dec. 10, 2001, now issued as U.S. Pat. No. 6,808,884; which claims the benefit under 35 USC § 119(e) to U.S. Application Ser. No. 60/254,497 filed Dec. 8, 2000, now abandoned. The disclosure of each of the prior applications is considered part of and is incorporated by reference in the disclosure of this application.

STATEMENT AS TO FEDERALLY SPONSORED RESEARCH

This invention resulted from research funded in whole or part by the National Institutes of Health, Grant No. GM33309. The Federal Government may have certain rights in this patent.

FIELD OF THE INVENTION

This invention relates generally to the fields of inorganic and nucleotide chemistry. More specifically, the invention relates to sterically demanding nucleotide intercalating compounds and methods for detecting base pair mismatches in nucleic acid sequences.

BACKGROUND

DNA base-pair mismatches arise during the course of genetic recombination and replication as a consequence of enzymatic errors or DNA damage. In the cell, complex systems exist to recognize, remove, and repair these mistakes to preserve the integrity of the genetic code. In certain diseases, particularly cancer, these repair systems fail and mismatches persist in a diseased cell's DNA. The design of molecules and systems to recognize site specific mismatches in DNA is an attractive experimental goal both for genetic screening and for the design of new chemotherapeutics. Existing strategies include assays using isolated mismatch recognition proteins, hybridization of oligonucleotide-fluorescent probe conjugates, electrophoretic/DNA chip methods, and differential chemical cleavage with reagents assaying for base accessability either in solution or the solid phase. None of these methods are ideal for detection of mismatches in the laboratory, and no strategies exist for using the presence of base-pair mismatches as a way of selectively treating disease.

Accordingly, there is a need for compositions and methods useful for recognizing site specific base-pair mismatches in polynucleotide duplexes.

SUMMARY OF THE INVENTION

The present invention is based on the discovery of a new class of sterically demanding metallo-intercalators. These compounds intercalate between bases in a duplex polynucleotide, but only where the bases are not fully complementary, for example, where there is a base-pair mismatch. The compounds are sufficiently sterically demanding that intercalation between bases in fully complementary duplexes does not occur to a significant degree. These mismatch intercalators are useful for detecting DNA and RNA defects, for diagnosing disorders characterized by the presence or increase in DNA and/or RNA defects, and for treating such disorders. The compounds of the invention are useful for SNP (single-nucleotide polymorphism) discovery. The compounds are also useful as carriers of cytotoxic agents targeting cells having deficient repair mechanisms (e.g., in various cancer cells).

A new class of compounds of the formula $M(R_1)(R_2)(R_3)^{3+}$ and derivatives thereof is described herein. Invention compounds intercalate only between nucleotide bases in the presence of a base-pair mismatch, and are therefore useful for detecting single base-pair mismatches. Further, the compounds are capable of catalyzing photolytic cleavage of nucleic acids at relatively long wavelengths, and under normal sunlight.

In accordance with the present invention, there are provided compounds of the formula $M(R_1)(R_2)(R_3)^{3+}$ and derivatives thereof In another aspect of the invention there are provided compositions comprising two complementary oligonucleotide strands having a base-pair mismatch, and compounds of the formula $M(R_1)(R_2)(R_3)^{3+}$.

In a further aspect of the invention, there are provided methods for determining the presence of a base-pair mismatch in a polynucleotide duplex, methods for diagnosing genetic disorders characterized by the presence or increased presence of DNA and/or RNA defects (for example base-pair mismatches), methods for treating disorders characterized by the presence or increased presence of DNA and/or RNA defects, and methods for screening agents for their ability to damage nucleic acid duplexes.

In a still further aspect of the invention, the compounds are useful for labeling or indicating base-pair mismatches. In yet another aspect of the invention, the compounds are capable of catalyzing cleavage of a polynucleotide duplex having a base-pair mismatch. In a further aspect of the invention, the compounds are useful for diagnosing and/or treating disorders characterized by the presence of base-pair mismatches in nucleic acid duplexes.

DETAILED DESCRIPTION OF THE INVENTION

Figure 1:
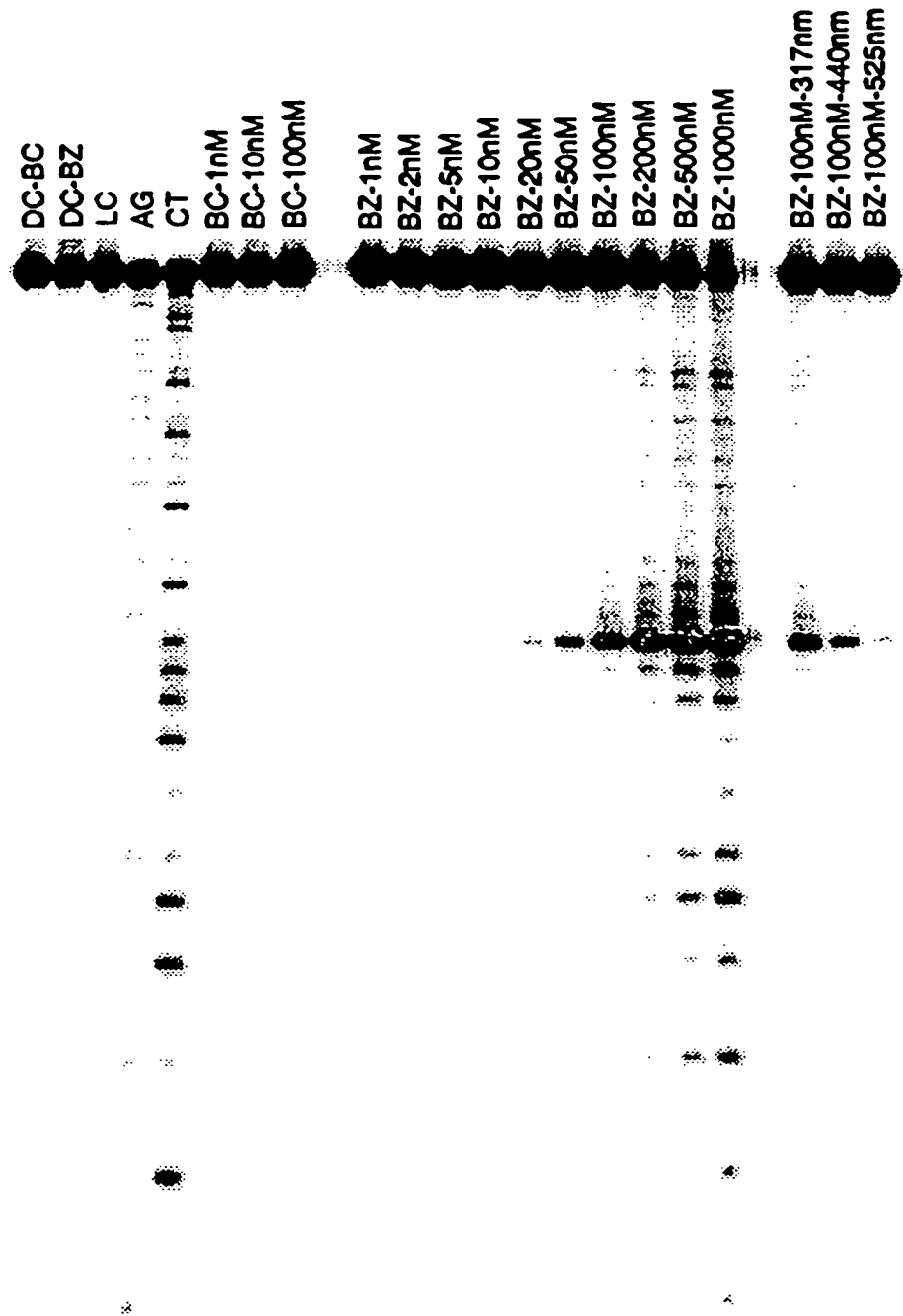
FIG. 1 displays the results of a comparative study of the base-pair mismatch detection ability of two sterically demanding metallo-intercalators of the invention, [Rh(bpy)$_2$chrysi] (BC) and [Rh(bpy)$_2$phzi] (BZ).
Figure 2:
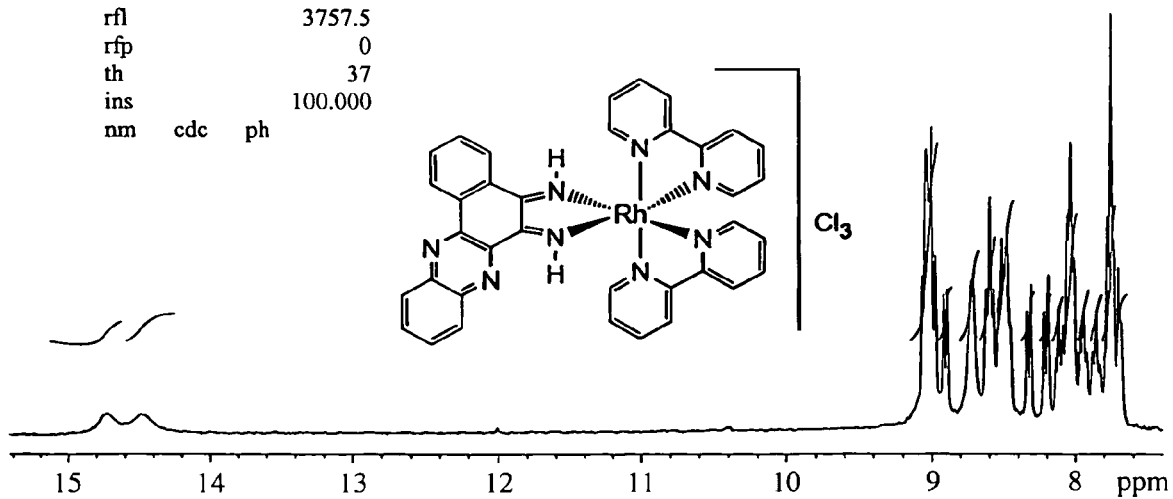
FIG. 2 contains a line drawing of invention compound [Rh(bpy)$_2$phzi]Cl$_3$ and its $^1$H NMR spectrum in CDCl$_3$.

The methods and compositions described herein provide a mutation/polymorphism detection system having the advantages of (a) simplicity, (b) accuracy, and (c) ability to detect all single base mismatches. The present invention also provides a method for detecting nucleic acid duplex mismatches in a sample, which is useful for screening normal or tumor cells for mismatch repair deficiencies. Such assays are important in the diagnosis of susceptibility to certain types of pathological conditions, for example, cancer.

Mismatches, according to the present invention, are hybridized nucleic acid duplexes in which the two strands are not 100% complementary. Lack of total homology may be due to deletions, insertions, inversions or substitutions. Mismatches between DNA-DNA, DNA-RNA or RNA-RNA duplexes can be detected using the methods and compounds of the invention. In addition, the presence of proteins binding to nucleic acid duplexes can be determined using the compounds and methods of the invention.

The ability to detect mismatches in coding and non-coding DNA, as well as RNA, is important in a number of diagnostic as well as therapeutic contexts. Such a mismatch may occur at a single nucleotide or over multiple nucleotides, and may result from a frame shift, stop codon, or substitution in a gene, each of which can independently render an encoded protein inactive. Alternatively, the mismatch may indicate a genetic variant which is harmless, resulting in a protein product with no detectable change in function (for example, a harmless gene polymorphism). Eight single base mismatches are possible, and these include G:A, C:T, C:C, G:G, A:A, T:T, C:A, and G:T, with U being substituted for T when the nucleic acid strand is RNA. Nucleic acid loops can form when at least one strand of a mismatch-containing sequence, or heteroduplex, includes a deletion, substitution, insertion, transposition, or inversion of DNA or RNA, for example.

Because many human diseases arise by single base pair changes in genes, the analysis of base pair mismatches and mutation has important implications in biomedical research and in medicine. For example, single base mutations at codons 12, 13 or 61 of one of the three ras genes occur in a significant number of human cancers, the highest incidence being found in adenocarcinomas of the pancreas (90%), the colon (50%) and lung (30%), in thyroid tumors (50%) and in myeloid leukemia (30%). (Bos, Canc. Res., 49:4682-4689, 1989). A considerable number of human genetic diseases are known to be caused by point mutation.

The present invention provides a highly sensitive and accurate method based on an assay using bulky intercalative compounds to determine the presence and location of a single or multiple base-pair mismatches. The present invention is particularly useful in the diagnosis of genetic diseases that arise from point mutations. For example, many cancers can be traced to point mutations in kinases, growth factors, receptors binding proteins and/or nuclear proteins. Other diseases that arise from genetic disorders include cystic fibrosis, Bloom's syndrome, thalassemia and sickle cell disease. In addition, several specific genes associated with cancer, such as DCC, NF-1, RB, p53, erbA and the Wilm's tumor gene, as well as various oncogenes, such as abl, erbB, src, sis, ras, fos, myb and myc have already been identified and examined for specific mutations.

The present invention provides methods for detecting single or multiple point mutations. One important distinction between the present invention methods and other known methods for identifying base-pair mismatches or mutations is that the method of the invention is based on the differences in base-stacking of the mismatches. The method is independent of the sequence composition of the hybridized duplex, as opposed to existing methods that depend on thermodynamic differences in hybridization. Furthermore, this method is nonhazardous, inexpensive, and can be used in a wide variety of applications, alone or in combination with other hybridization-dependent methods.

The present invention also relates to the choice of nucleic acid to be tested. Any nucleic acid, DNA or RNA, can be subjected to this mismatch detection method. The nucleic acid to be studied may comprise natural or synthetic sequences encoding up to the entire genome of an organism. The nucleic acid can be obtained from any source, for example, from plasmids, cloned DNA or RNA, or from natural DNA or RNA from any source, including bacteria, yeast, viruses, organelles and higher organisms such as plants and animals. The samples may be extracted from tissue material or cells, including blood cells, amniocytes, bone marrow cells, cells obtained from a biopsy specimen and the like, by a variety of techniques as described for example by Maniatis et al., *Molecular Cloning: A Laboratory Manual,* Cold Spring Harbor Laboratory Cold Spring Harbor, N.Y. (1982), incorporated herein by reference.

Alternatively, the sequences of choice can also be prepared by well known synthetic procedures. For standard DNA and RNA synthesis methods, see for example "Synthesis and Applications of DNA and RNA" ed. S. A. Narang, Academic Press, 1987, M. J. Gait, "Oligonucleotide Synthesis", IRL Press, Wash. D.C. U.S.A., 1984, and "Oligonucleotides and Analogues" ed. F. Eckstein, IRL Press, Wash. D.C. U.S.A., 1991, as incorporated herein by reference. Briefly, oligonucleotides and oligonucleotide analogs may be synthesized, conveniently through solid state synthesis of known methodology. In a preferred embodiment, the monomeric units are added to a growing oligonucleotide chain which is covalently immobilized to a solid support. Typically, the first nucleotide is attached to the support through a cleavable linkage prior to the initiation of synthesis. Step-wise extension of the oligonucleotide chain is normally carried out in the 3' to 5' direction. When the synthesis is complete, the polymer is cleaved from the support by hydrolyzing the linkage mentioned above and the nucleotide originally attached to the support becomes the 3' terminus of the resulting oligomer. Nucleic acid synthesizers such as the Applied Biosystems, Incorporated 380B are commercially available and their use is generally understood by persons of ordinary skill in the art as being effective in generating nearly any oligonucleotide or oligonucleotide analog of reasonable length which may be desired. Triester, phosphoramidite, or hydrogen phosphonate coupling chemistries are used with these synthesizers to provide the desired oligonucleotides or oligonucleotide analogs.

Methods and conditions used for contacting the oligonucleotide strands of two DNAs, two RNAs or one DNA and one RNA molecule'under hybridizing conditions are widely known in the art. Suitable hybridization conditions may be routinely determined by optimization procedures well known to those skilled in the art to establish protocols for use in a laboratory. See e.g., Ausubel et al., *Current Protocols in Molecular Biology*, Vol. 1-2, John Wiley & Sons (1989); Sambrook et al., Molecular Cloning A Laboratory Manual, 2nd Ed., Vols. 1-3, Cold Springs Harbor Press (1989); and Maniatis et al., *Molecular Cloning: A Laboratory Manual,* Cold Spring Harbor Laboratory Cold Spring Harbor, N.Y. (1982), all of which are incorporated by reference herein. For example, conditions such as temperature, concentration of components, hybridization and washing times, buffer components, and their pH and ionic strength may be varied.

In one particular application, the methods and compounds of the invention provide mismatch detection techniques for identifying or evaluating mutations in nucleic acid sequences. Mutations are heritable changes in the sequence of the genetic material of an organism which can cause fatal defects like hereditary diseases or cancer (Modrich, Science 266:1959-1960, 1994). As a result, methods for mutation detection are gaining increasing importance especially in medical diagnostics. Although mutations can be localized with great precision by DNA sequencing (Sanger et al. Proc.

Natl. Acad. Sci. USA 74:5463-5467, 1977), this procedure is relatively time consuming and expensive.

The present invention provides, in one embodiment, methods and compositions that measure mutations by mismatches in heteroduplex DNAs obtained after annealing wild-type with mutant sequences in vitro. By the term "heteroduplex" is meant a structure formed between two annealed, complementary nucleic acid strands (e.g., the annealed strands of test and reference nucleic acids) in which one or more nucleotides in the first strand are unable to appropriately base pair with those in the second opposing, complementary strand because of one or more mismatches. Examples of different types of heteroduplexes include those which exhibit an exchange of one or several nucleotides, and insertion or deletion mutations. The term "complementary," as used herein, means that two nucleic acids, e.g., DNA or RNA, contain a series of consecutive nucleotides which are capable of forming matched Watson-Crick base pairs to produce a region of double-strandedness. Thus, adenine in one strand of DNA or RNA pairs with thymine in an opposing complementary DNA strand or with uracil in an opposing complementary RNA strand. The region of pairing is referred to as a "duplex." A duplex may be either a homoduplex or a heteroduplex.

In accordance with the present invention, there are provided compounds having the formula:

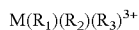

wherein:
  M is a suitable photoexcitable metal,
  $R_1$ and $R_2$ are ligands which are each independently ethylenediamine or a substituted derivative thereof, or substituted or unsubstituted aryl or heteroaryl of 1 to 5 rings, and
  $R_3$ is a ligand having the following structure:

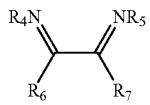

wherein:
  $R_4$ and $R_5$ are —H or lower alkyl,
  $R_6$ and $R_7$ are taken together to form a substituted or unsubstituted, fused aromatic or heteroaromatic ring system comprising at least four rings, wherein each ring contains from 0 to about 3 heteroatoms; and
  wherein substituents on said substituted rings are —H, —R, halo, —OH, —OR, —NH$_2$, —NHR, —NR$_2$, —CN, —NO$_2$, —SH, —SO$_3$, —OSO$_3$, —C(O)OH, —C(O)OR, —C(O)NH$_2$, —C(O)NHR, —C(O)NR$_2$, —SO$_3$R, or —OSO$_3$R, wherein each R is independently lower alkyl, cycloalkyl, lower alkenyl, lower alkynyl, or phenyl.

Suitable metals contemplated for use in the practice of the present invention include, for example, Rh, Ru, Co, Fe, Cr, Cu, Zn, Cd, or Pb.

$R_2$ contemplated for use in the practice of the present invention include, for example, alkyl, aryl, heteroaryl, halo, —OH, —OR, —NH$_2$, —NHR, —NR$_2$, —CN, —NO$_2$, —SH, —SO$_3$, —OSO$_3$, —C(O)OH, —C(O)OR, —C(O)NH$_2$, —C(O)NHR, —C(O)NR$_2$, —SO$_3$R, or —OSO$_3$R, wherein each R is independently lower alkyl, cycloalkyl, lower alkenyl, lower alkynyl, or phenyl.

In a particular embodiment, ligands $R_1$ and $R_2$ include a 5-phenanthrolyl substituent.

In particular embodiments, substituents on ligands $R_1$ and $R_2$ also include, for example, peptides, polypeptides, nucleic acids, nucleosides, nucleotides, and the like.

In preferred embodiments, M is Rh, $R_1$ and $R_2$ are each independently 2,2'-bipyridine, 4,4'-dimethyl-2,2'-bipyridine, or 4,4'-diamido-2,2'-bipyridine, and $R_3$ is a ligand having the structure:

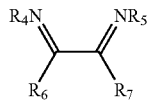

wherein $R_4$ and $R_5$ are —H, $R_6$ and $R_7$ are taken together to form a fused aromatic or heteromatic ring system comprising at least 4 rings, wherein each ring contains from 0 to about 2 heteroatoms.

In particularly preferred embodiments, $R_3$ has the following structure:

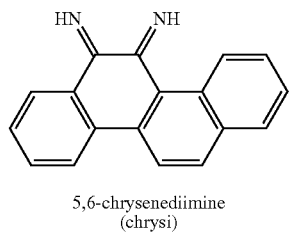

5,6-chrysenediimine
(chrysi)

In yet another preferred embodiment, $R_3$ has the following structure:

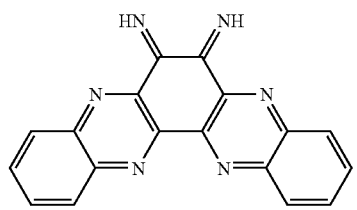

In a most preferred embodiment, M is Rh, $R_1$ and $R_2$ are each 2,2'-bipyridine and $R_3$ has the structure:

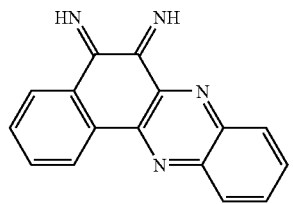

benzophenanzinediimine
(phzi)

The term "sterically demanding intercalating compound" or "sterically demanding intercalating agent" as used herein refers to a compound that is not capable of substantially intercalating between the bases of a normal or non-mismatched duplex polynucleotide, but is capable of intercalating between the bases of a duplex polynucleotide having an error and/or damage. A labeled agent is a sterically demanding intercalating agent having a detectable label, as defined below. A "cleaving" agent is a sterically demanding intercalating agent that is capable of cleaving or catalyzing the cleavage of a polynucleotide duplex in which it is intercalated. A "photocleaving" compound or agent is a sterically demanding intercalating agent capable of catalyzing photolysis of a polynucleotide in which it is intercalated.

The terms "damage" and "error" as used herein refer to a departure from the "normal" or non-mismatched or ideal structure of a polynucleotide duplex. In the "ideal" structure, all bases are paired with complementary bases, and no nicks, breaks, or gaps occur in the backbones. "Error" describes the condition in which a base is paired with a non-complementary base, or a base is absent from a position (abasic), or a gap exists in the sequence of one strand (e.g., the strands have different numbers of bases, and the unpaired location does not occur at the end of the strand). "Error" includes simple base-pair mismatches, for example in which a denatured DNA sample is hybridized with a substantially (but not completely) complementary oligonucleotide probe: the probe and target can depart from complementarity by one or more bases. "Damage" describes the condition in which the conformation of the duplex is perturbed, for example by a nick in the backbone, T-T dimerization, and the like.

In humans, each cell division requires the replication of approximately six billion bases of DNA. Most errors are detected and corrected by DNA repair enzymes. However, DNA repair enzymes are inactive or inefficient in some forms of cancer. These cancers can be diagnosed by the presence of higher than normal numbers of base-pair mismatches per cell. A "condition" or "disorder" characterized by polynucleotide damage or error is a pathological state that can be distinguished from a normal state by the presence of an increased level, rate, or concentration of damage and/or errors in polynucleotide duplexes. The increase in polynucleotide damage and/or error can be determined with respect to a control, or with respect to a known or previously measured rate established for "normal" individuals.

The process of mismatch repair of nucleic acids has also received considerable attention in recent years with the elucidation of systems in microorganisms such as *E. coli*, and more recently, mammals including humans. For example, continuous cellular damages occur to nucleic acids during the cell life cycle; for example damage resulting from exposure to radiation, or to alkylating and oxidative agents, spontaneous hydrolysis and errors during replication. Such damages must be repaired prior to cell division. There are a number of different cellular repair systems and a variety of components that participate in these systems. One component is represented by the class of DNA repair enzymes known as mismatch repair glycosylases. These enzymes convert mismatches in DNA to aldehyde-containing abasic sites. These abasic sites can also occur by other means. For example, they can occur spontaneously, or following deamination of cytosine to uracil and subsequent removal of uracil by uracil glycosylase. It has been estimated that almost 10,000 abasic sites are generated per cell per. Finally abasic sites are generated by DNA damaging agents such as ionizing radiation, reactive oxygen intermediates, antibiotics, bleomycin-iron complexes, neocarzinostatin or alkylation agents (methylmethanesulfonate, dimethylsulfate etc). Unrepaired abasic sites can be lethal or promutagenic lesions since during DNA replication DNA polymerases insert primarily adenines opposite them. Closely-spaced abasic sites generated within a few base pairs of each other by damaging agents may be a particularly significant set of lesions, as they may hinder repair, or they can be enzymatically converted to double strand breaks or other complex multiply-damaged sites. It has been postulated that such complex forms of DNA damage may be particularly difficult for cells to overcome. Quantification of the overall number of abasic sites directed to looking at abasic sites resulting from DNA damage has been reported. The present invention compounds and methods of use are suitable for identification of cells having mismatch repair defects. Further, a cytotoxic compound can be attached or linked to a compound of the invention for delivery of the cytotoxic compound to a cell, such as a cancer cell, having a repair system defect.

Having identified the presence of a cancer or other pathologic base-pair mismatch related condition in a subject, a compound of the invention can be administered linked or attached to a cytotoxic agent such as ricin A chain or a cancer chemotherapeutic agent to the subject in order to enhance the therapeutic efficacy of the agent in the subject. A therapy modulating agent such as a chemosensitizing agent or a radiomodulating agent also can be a useful therapeutic agent where a subject is to be treated by radiotherapy. A radiomodulating agent, for example, can be a radiosensitizer, which can be administered with a particular invention compound to sensitize a tumor to the effects of radiation.

The term "aryl" as used herein refers to a moiety having one to about five rings, of which at least half are aromatic. Exemplary aryl groups include, without limitation, phenyl, naphthyl, biphenyl, terphenyl, 2-phenyl-naphthyl, anthryl, phenanthryl, fluorenyl, indanyl, cholanthrenyl, acephenanthrenyl, and the like.

The term "heteroaryl" as used herein refers to an aryl moiety having one or more heteroatoms, preferably no more than about three heteroatoms per ring. Heteroatoms can include, for example, oxygen, sulfur, nitrogen, boron, and phosphorus. Exemplary heteroaryl groups include pyridyl, pyrazinyl, indolyl, cinnolinyl, carbazolyl, acridinyl, quinazolinyl, purinyl, benzofuranyl, benzothienyl, quinolyl, phenothiazinyl, and the like.

The terms "substituted aryl" and "substituted heteroaryl" refer to aryl and heteroaryl moieties as described above, further having at least one substituent. Substituted aryl and substituted heteroaryl preferably have no more than about four substituents per ring, preferably no more than three per ring. Suitable substituents include —H, —R, halo, —OH, —OR, —NH$_2$, —NHR, —NR$_2$, —CN, —NO$_2$, —SH, —SO$_3$, —OSO$_3$, —C(O)OH, —C(O)OR, —C(O)NH$_2$, —C(O)NHR, —C(O)NR$_2$, —SO$_3$R, or —OSO$_3$R, wherein each R is independently lower alkyl, cycloalkyl, lower alkenyl, lower alkynyl, or phenyl.

The term "halo" refers to fluoro, chloro, bromo, and iodo.

The term "alkyl" refers to a fully saturated branched or unbranched hydrocarbon moiety. The term "lower alkyl" refers to an alkyl moiety having from one to about six carbon atoms. Suitable lower alkyl radicals include methyl, ethyl, propyl, isopropyl, butyl, but-2-yl, hexyl, and the like.

The term "cycloalkyl" refers to a saturated hydrocarbon radical having one to three rings, and containing from three to about nine carbon atoms in the ring structure. Suitable cycloalkyl moieties include cyclopropyl, cyclobutyl, cyclopentyl, cyclohexyl, 3-methylcyclohexyl, bicyclooctyl, norbornyl, and the like.

The term "alkenyl" refers to a straight, branched, or cyclic hydrocarbon radical that includes a double bond, but does not include a triple bond. The term "lower alkenyl" refers to an alkenyl radical having from two to about six carbon atoms. Suitable lower alkenyl moieties include, without limitation, vinyl, allyl, 2-butenyl, cyclohexenyl, and the like.

The term "alkynyl" refers to a straight, branched, or cyclic hydrocarbon radical that includes a triple bond. The term "lower alkynyl" refers to an alkynyl radical having from two to about six carbon atoms. Suitable lower alkynyl moieties include, without limitation, acetenyl, 2-propynyl, 3-butynyl, and the like.

"Arylalkyl" means an alkyl residue attached to an aryl ring. Examples are benzyl, phenethyl and the like.

"Heteroarylalkyl" means an alkyl residue attached to a heteroaryl ring. Examples include, e.g., pyridinylmethyl, pyrimidinylethyl and the like.

The term "bpy" refers to 2,2'-bipyridine.

The term "phen" refers to 1,10-phenanthroline.

The term "effective amount" refers to the amount of compound necessary to cause cleavage of an polynucleotide duplex having a base mismatch when subjected to light of sufficient energy. The minimum effective amount can vary depending on reaction conditions and the identity of the bases involved in the mismatch, but in general will range from a ratio of about 100:1 to about 1:1 nucleotide:compound. The effective amount for a particular application can vary with the conditions employed, but can be determined using only routine experimentation.

The term "label" as used herein refers to a moiety that is detectable or can be manipulated to provide a detectable signal. Suitable detectable labels include radioactive atoms such as $^3$H, $^{14}$C, and the like, fluorophores, chromophores, electron-dense reagents, isotopic labels, enzymes capable of catalyzing signal reactions such as chromogenic, luminescent, and fluorescent reactions, binding ligands, cleaving molecules, and the like. "Binding ligands" are moieties capable of binding a labeled compound or a solid support; for example, a detectable label can comprise a moiety capable of binding a polynucleotide duplex to a solid support, where the polynucleotide can be detected directly, for example by PCR or hybridization assays. Alternatively, a binding ligand can bind to another compound which includes a detectable label, for example an enzyme-labeled antibody. Cleaving molecules are capable of cleaving, or catalyzing the cleavage of, polynucleotides; this can serve as a label by, for example, releasing one end of a duplex polynucleotide from a surface-bound complex. One can detect the released ends, for example by end-labeling the strands prior to cleavage, or can detect the newly cleaved end bound to the support, for example where the duplexes are end-protected prior to cleavage, and subject to enzymatic degradation in the absence of the end protecting group.

The term "cleavage conditions" refers to reaction conditions sufficient to cause cleavage on at least one strand of a polynucleotide duplex having a base mismatch in the presence of an effective amount of a compound of the invention. "Photocleavage conditions" are those conditions sufficient to cause photolysis of a polynucleotide in the presence of an effective amount of photocleaving compound or agent.

The term "mutagenic agent" refers to a physical, chemical, or biological agent capable of causing DNA and/or RNA damage or errors. Examples of known mutagenic agents include ionizing radiation, ultraviolet light, 2-aminopurine, 5-bromouracil, hydroxylamine, nitrous acid, ethyl ethane sulfonate, nitrosamines, nitrogen mustard, acridine, proflavin, and the like.

The term "base-stacking perturbations" refers to any event that causes a perturbation in base-stacking such as, for example, a base-pair mismatch, a protein binding to its recognition site, an abasic site, a bulge, or any other entities that form oligonucleotide adducts.

The term "base flipping" refers to the process by which a target nucleic acid base is flipped out of the double helix, making that base accessible for reaction.

The term "denaturing" refers to the process by which strands of oligonucleotide duplexes are no longer base-paired by hydrogen bonding and are separated into single-stranded molecules. Methods ccof denaturation are well known to those skilled in the art and include thermal denaturation and alkaline denaturation.

The term "hybridized" refers to two nucleic acid strands associated with each other which may or may not be fully base-paired.

The term "intercalative moieties" refers to planar aromatic or heteroaromatic moieties that are capable of partial insertion and stacking between adjacent base pairs of double-stranded oligonucleotides. These moieties may be small molecules or part of a larger entity, such as a protein.

The term "lesion" refers to an abnormal change in structure of DNA or RNA. The lesions may include mutations and mismatches in the DNA or RNA and may be naturally occurring, or non-naturally occurring.

The term "mismatches" refers to nucleic acid bases within hybridized duplexes which are not 100% complementary. A mismatch includes any incorrect pairing between the bases of two nucleotides located on complementary strands of DNA that are not the Watson-Crick base-pairs A:T or G:C. The lack of total homology may be due to deletions, insertions, inversions, substitutions or frameshift mutations.

The term "mutation" refers to a sequence rearrangement within DNA. The most common single base mutations involve substitution of one purine or pyrimidine for the other (e.g., A for G or C for T or vice versa), a type of mutation referred to as a "transition". Other less frequent mutations include "transversions" in which a purine is substituted for a pyrimidine, or vice versa, and "insertions" or "deletions", respectively, where the addition or loss of a small number (1, 2 or 3) of nucleotides arises in one strand of a DNA duplex at some stage of the replication process. Such mutations are also known as "frameshift" mutations in the case of insertion/deletion of one of two nucleotides, due to their effects on translation of the genetic code into proteins. Mutations involving larger sequence rearrangement also may occur and can be important in medical genetics, but their occurrences are relatively rare compared to the classes summarized above.

The term "nucleoside" refers to a nitrogenous heterocyclic base linked to a pentose sugar, either a ribose, deoxyribose, or derivatives or analogs thereof. The term "nucleotide" relates to a phosphoric acid ester of a nucleoside comprising a nitrogenous heterocyclic base, a pentose sugar, and one or more phosphate or other backbone forming groups; it is the monomeric unit of an oligonucleotide. Nucleotide units may include the common bases such as guanine (G), adenine (A), cytosine (C), thymine (T), or derivatives thereof. The pentose sugar may be deoxyribose, ribose, or groups that substitute therefore.

The terms "nucleotide analog", "modified base", "base analog", or "modified nucleoside" refer to moieties that function-similarly to their naturally occurring counterparts but have been structurally modified.

The terms "oligonucleotide" or "nucleotide sequence" refers to a plurality of joined nucleotide units formed in a specific sequence from naturally occurring heterocyclic bases and pentofuranosyl equivalent groups joined-through phosphorodiester or other backbone forming groups.

The terms "oligonucleotide analogs" or "modified oligonucleotides" refer to compositions that function similarly to natural oligonucleotides but have non-naturally occurring portions. Oligonucleotide analogs or modified oligonucleotides may have altered sugar moieties, altered bases, both altered sugars and bases or altered inter-sugar linkages, which are known for use in the art.

Hybridization of polynucleotides, oligonucleotides, probes and/or primers to target sequences proceeds according to well-known and art-recognized base-pairing properties, such that adenine base-pairs with thymine or uracil, and guanine base-pairs with cytosine. The property of a nucleotide that allows it to base-pair with a second nucleotide is called complementarity. Thus, adenine is complementary to both thymine and uracil, and vice versa; similarly, guanine is complementary to cytosine and vice versa. An oligonucleotide which is complementary along its entire length with a target sequence is said to be perfectly complementary, perfectly matched, or fully complementary to the target sequence, and vice versa. An oligonucleotide and its target sequence can have related sequences, wherein the majority of bases in the two sequences are complementary, but one or more bases are noncomplementary, or mismatched. In such a case, the sequences can be said to be substantially complementary to one another. If the sequences of an oligonucleotide and a target sequence are such that they are complementary at all nucleotide positions except one, the oligonucleotide and the target sequence have a single nucleotide mismatch with respect to each other.

Conditions for hybridization are well-known to those of skill in the art and can be varied within relatively wide limits. Hybridization stringency refers to the degree to which hybridization conditions disfavor the formation of hybrids containing mismatched nucleotides, thereby promoting the formation of perfectly matched hybrids or hybrids containing fewer mismatches; with higher stringency correlated with a lower tolerance for mismatched hybrids. Factors that affect the stringency of hybridization include, but are not limited to, temperature, pH, ionic strength, and concentration of organic solvents such as formamide and dimethylsulfoxide. As is well known to those of skill in the art, hybridization stringency is increased by higher temperatures, lower ionic strengths, and lower solvent concentrations. See, for example, Ausubel et al., supra; Sambrook et al., supra; M. A. Innis et al. (eds.) PCR Protocols, Academic Press, San Diego, 1990; B. D. Hames et al. (eds.) Nucleic Acid Hybridisation: A Practical Approach, IRL Press, Oxford, 1985; and van Ness et al., (1991) Nucleic Acids Res. 19:5143-5151. An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Thus, in the formation of hybrids (duplexes) between an oligonucleotide and its target sequence, the oligonucleotide is incubated in solution, together with a polynucleotide containing the target sequence, under conditions of temperature, ionic strength, pH, etc, that are favorable to hybridization, i.e., under hybridization conditions. Hybridization conditions are chosen, in some circumstances, to favor hybridization between two nucleic acids having perfectly-matched sequences, as compared to a pair of nucleic acids having one or more mismatches in the hybridizing sequence. In other circumstances, hybridization conditions are chosen to allow hybridization between mismatched sequences, favoring hybridization between nucleic acids having fewer mismatches.

The degree of hybridization of an oligonucleotide to a target sequence, also known as hybridization strength, is determined, by methods that are well-known in the art. A preferred method is to determine the $T_m$ of the hybrid duplex. This is accomplished by subjecting a duplex in solution to gradually increasing temperature and monitoring the denaturation of the duplex, for example, by absorbance of ultraviolet light, which increases with the unstacking of base pairs that accompanies denaturation. $T_m$ is generally defined as the temperature midpoint of the transition in ultraviolet absorbance that accompanies denaturation. Alternatively, if $T_m$'s are known, a hybridization temperature (at fixed ionic strength, pH and solvent concentration) can be chosen that is below the $T_m$ of the desired duplex and above the $T_m$ of an undesired duplex. In this case, determination of the degree of hybridization is accomplished simply by testing for the presence of hybridized probe.

The term "stringent conditions" refers to polynucleotide hybridization conditions (generally a combination of temperature, concentration, and denaturing agent) under which a probe oligonucleotide will bind to a target polynucleotide only if completely complementary. "Non-stringent conditions" are hybridization conditions which tolerate the presence of one or more base-pair mismatches, i.e., where substantially complementary polynucleotides will hybridize. Substantially complementary polynucleotides can differ from exact complementarity in 5% or more of the base positions, or can contain a few as a single base-pair mismatch.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

In its most fundamental form, the present invention is directed to a method and compositions useful for detecting in a test polynucleotide sample, preferably DNA, the presence of a heteroduplex having a single base pair mismatch or a deletion or addition of nucleotides.

The techniques described herein are extremely useful for detecting DNA mutations and polymorphisms associated with mammalian diseases (such as cancer and various inherited diseases), as well as mutations which facilitate the development of therapeutics for their treatment. Alternatively, the methods are also useful for forensic applications or the identification of useful traits in commercial (for example, agricultural) species.

The methods of the invention are useful for any pair of mutant and wildtype nucleic acids wherein heteroduplexes can be prepared. Non-limiting examples of uses for the methods of the invention include detection of disease-related mutations, including genetic diseases, diseases related to inherited or inborn errors of metabolism, other inherited disorders such as cystic fibrosis, Huntington's disease, muscular dystrophy, hemophilia, thalassemia, sickle cell anemia, neurofibromatosis and all malignancies. Other useful applications of the methods of the invention include screening and detection of the products of in vitro mutagenesis, identification of new disease genes, identification of new genetic markers such as mini- or microsatellite DNA, or polymorphisms such as restriction fragment linked polymorphisms (RFLP) and detection of SNPs. The methods of the invention are also useful in basic medical research, including identification of sequence information and mutations using human nucleic acid sequences obtained, for example, from the efforts of the Human Genome Project; measurement of polymorphisms in humans at newly-isolated genetic loci; and the establishment of genetic markers comprising DNA sequence polymorphisms, which are in turn useful for developing physical and genetic maps of chromosomal DNA. These characterizations can be suitably applied to plants, animals including humans, and microorganisms (including viruses).

Standard reference works setting forth the general principles of recombinant DNA technology and cell biology, and describing conditions for isolation and handling of nucleic acids, denaturing and annealing nucleic acids, hybridization assays, and the like, include: Sambrook, J. et al., MOLECULAR CLONING: A LABORATORY MANUAL, 2nd Edition, Cold Spring Harbor Press, Cold Spring Harbor, N.Y., 1989; Albers, B. et al., MOLECULAR BIOLOGY OF THE CELL, 2nd Ed., Garland Publishing, Inc., New York, N.Y., 1989; Watson, J. D., et al., MOLECULAR BIOLOGY OF THE GENE, Volumes I and II, Benjamin/Cummings Publishing Co., Inc., Menlo Park, Calif., 1987; Darnell, J. E. et al., MOLECULAR CELL BIOLOGY, Scientific American Books, Inc., New York, N.Y., 1986; Lewin, B. M., GENES II, John Wiley & Sons, New York, N.Y.,1985, which references are hereby incorporated by reference in their entirety.

One aspect of the invention is based on the discovery that one can prepare intercalating compounds that are too sterically demanding to intercalate between the bases of a "normal" polynucleotide duplex, but can intercalate between the bases of a duplex in the presence of damage or error. Such compounds are useful for indicating the presence of polynucleotide damage or error, for diagnosing conditions characterized by polynucleotide damage or error, for separating or isolating damaged or erroneous polynucleotides, and for treating conditions characterized by polynucleotide damage or error.

One aspect of the invention is a method for determining the existence of a difference between a target polynucleotide and a probe oligonucleotide. Previous methods for detecting a base mismatch between a probe and a target relied on sensitive adjustment of hybridization conditions (e.g., temperature and concentration), such that hybridization occurred only where the probe and target were completely complementary, and not otherwise ("stringent conditions"). Using sterically demanding intercalating compounds, however, one can directly label polynucleotide duplexes having a base-pair mismatch, and thus directly detect lack of full complementarity between a probe and a target under non-stringent conditions, moderately stringent conditions, or highly stringent conditions. Thus, in one embodiment of the invention, a sample containing a target polynucleotide is provided, contacted with a probe oligonucleotide under non-stringent conditions, moderately stringent conditions, or highly stringent conditions, contacted with a labeled hindered intercalating compound, and the product duplex nucleic acids examined for the presence of a label or cleavage products. This method can be used, for example, to diagnose hereditary differences and/or the presence of genetic defects, to diagnose disease or risk of disease (e.g, cell proliferative disorders such as neoplasms and/or cancers), to distinguish between different strains of pathogenic organisms, to establish paternity, to distinguish between a subject's DNA and DNA found in a forensic sample, amongst other uses. The sample/target polynucleotide can be provided in single strand or double strand form, but is preferably denatured prior to hybridization with the probe oligonucleotide. The probe oligonucleotide can be as short as about 8-10 bases or as long as several thousand bases. Indeed, the probe can be as long or longer than the target polynucleotide.

A sample to be assayed can be in any medium of interest, and will generally be a sample of medical, veterinary, environmental, nutritional, or industrial significance. Human and animal specimens and biological fluids particularly can be assayed by the present method, providing that they contain nucleic acids or cells from which nucleic acids can be prepared. Preferred sources include blood, sperm, other tissue (particularly tumor tissue or cells), milk, urine, cerebrospinal fluid, sputum, fecal matter, lung aspirates, throat swabs, genital swabs and exudates, rectal swabs, and nasopharyngeal aspirates. Accordingly, the nucleic acid, preferably DNA, being analyzed can be obtained from any source, including blood cells, tumor tissues, cells in culture or any tissue, and can be obtained from any species including humans.

The method can be facilitated by binding the target, probe, or intercalating compound to a solid support, to simplify washing and purification. Thus, for example, one can provide a solid support (such as a microwell format plate, dipstick, membrane or other surface) having a probe immobilized on the surface. If desired, the complementary portion of the probe can be attached to a spacer, to permit the probe to interact with the target polynucleotide away from the support surface. The sample polynucleotide is added or spotted on the support, and allowed to hybridize with the probe under non-stringent conditions. The surface is then washed to remove any non-hybridized material, contacted with a sterically demanding intercalating agent, and washed again to remove any non-bound compound. If the probe and target are exactly complementary, the sterically demanding intercalating compound does not bind, and no signal appears. If at least one base-pair mismatch is present, the compound intercalates and provides a detectable signal. Optionally, one can use a cleaving agent, for example a photocleaving agent of the invention, and detect the presence of base pair mismatches by exposing the bound duplexes to cleaving conditions, eluting any released oligonucleotides, and sizing the resulting fragments, for example by polyacrylamide gel electrophoresis (PAGE). Knowledge of the probe sequence and the size of the released fragment permits one to determine the position of the base-pair mismatch.

In another embodiment of the present invention, oligonucleotides are used in procedures which utilize arrays of oligonucleotides, such as array-based analysis of gene expression. In this embodiment, an ordered array of oligonucleotides of different known sequences is used as a platform for hybridization to one or more test polynucleotides, nucleic acids or nucleic acid populations. Oligonucleotides comprising the wild-type sequence and all possible mutant sequences for a given region of a gene of interest can be placed on an array. Exposure of the array to DNA or RNA from a subject or biological specimen, under hybridization conditions, followed by contacting the array with a sterically hindered intercalating agent of the invention allows determination of wild-type or mutant status for the gene of interest. See, for example, U.S. Pat. Nos. 5,492,806; 5,525,464; 5,556,752; and PCT Publications WO 92/10588 and WO 96/17957. The intercalating agent will only intercalate at sites of nucleic acid mismatch (e.g., T-T, C-C, A-A, A-C, G-T, and the like). This technique allows discrimination of fully complementary sequences and sequences having a single-nucleotide differences. Materials for construction of arrays include, but are not limited to, nitrocellulose, glass, silicon wafers, optical fibers and other materials suitable for construction of arrays such as are known to those of skill in the art.

The types of mutations that can be detected by the present methods include both homozygous and heterozygous mutations. Heterozygosity means the presence on one of a pair of homologous chromosomes of a DNA sequence difference. Depending upon the context, such a sequence difference is commonly referred to as a mutation ("heterozygous mutation") or as an alternative "allele" for a given genetic locus. By definition, heterozygosity only exists in DNA of a diploid organism.

However, the present methods are not limited to testing heterozygous or diploid organisms, because any detectable sequence difference among a population of DNA molecules in a sample will produce a mismatched or mispaired heteroduplex that can be screened for, or detected, using sterically hindered intercalating compounds of the invention. In other words, the principle underlying the detection of homozygous mutations by the present methods is applicable to viral or bacterial DNA sequences or other non-diploid DNA species.

In another aspect of the invention there are provided methods for detecting DNA damage or errors existing in a cell, by contacting the DNA with a labeled sterically demanding intercalating compound, and determining whether or not the compound binds to DNA in the cell. This method is useful for detecting or diagnosing conditions characterized by increased DNA damage and/or errors, such as congenital defects in DNA repair or error-correction enzymes, cancer, and the like. Further, the method is useful for determining and quantifying mutagenic effects of other compounds on a given host cell, for example, by determining the "natural" error/damage rate for a host cell population, exposing a population of host cells to a potential mutagenic agent, contacting the cell with a labeled sterically demanding intercalating compound, and determining whether or not the compound binds to DNA in the cell.

Intracellular labeling can be detected by standard means, for example, by detecting fluorescence of a labeled intercalating compound. Detectable labels or tags suitable for use with the compounds of the invention are well-known to those of skill in the art and include, but are not limited to, radioactive isotopes, chromophores, fluorophores, chemiluminescent and electrochemiluminescent agents, magnetic labels, immunologic labels, ligands and enzymatic labels. Alternatively, one can employ a cleaving compound, and effect cleavage of any intercalated DNA. The cell can then be lysed, and the resulting DNA fragments sized (and compared to controls).

Sterically demanding intercalating compounds can be prepared starting from known intercalating compounds and principles, by adding sterically bulky groups to the compound until it is incapable of intercalating in normal polynucleotide duplexes. One can screen for such compounds by providing a library containing a plurality of potential sterically demanding intercalating compounds, and providing a substrate with a plurality of normal duplexes and a plurality of damaged or erroneous duplexes (e.g., duplexes having one or more base mismatches, preferably of several different sequences). The compounds are first applied to the normal duplexes, and all compounds that intercalate are eliminated. The remainder are then applied to the damaged duplexes, and the compounds that intercalate are separated and/or identified to provide sterically demanding intercalating compounds. This set of compounds can be further screened for photolytic activity by exposing the compound-duplex complexes to light of sufficient energy for varying periods of time, and identifying any compounds released by photolysis. Thus, in one embodiment, the invention provides a library of sterically demanding intercalating compounds having the general formula $M(R_1)(R_2)(R_3)^{3+}$, as described herein.

Sterically demanding intercalating compounds can be labeled by a variety of methods known in the art. For example, the compounds can be prepared by incorporating radioactive atoms or electron-dense reagents. Alternatively, the compounds can be conjugated with fluorophores, chromophores, spin labels, enzymes, antibodies or ligands, and the like. Further, some sterically demanding intercalating compounds are intrinsically colored or fluorescent, and are thus "self-labeled." Additionally, some sterically demanding intercalating compounds exhibit a shift in peak fluorescence or color when intercalated (as compared with their solution state). Such compounds can be used in assays for detecting damaged or error-containing polynucleotide duplexes by adding the compound and monitoring the sample for appearance of the color or fluorescence peak that indicates an intercalated compound.

Active sterically demanding intercalating compounds can be used to diagnose and treat conditions characterized by the presence of a substantial number of polynucleotide errors or damaged locations. Diagnosis is accomplished by contacting a nucleic acid sample with a labeled sterically demanding intercalating compound, whether by introducing the compound into a cell or by extracting the nucleic acids from a cell. The product is examined for the number or quantity of errors or damage present, and is compared to a control sample or to an established standard or threshold. For example, one can obtain a biopsy, lyse the cells and extract the nucleic acids, add a labeled compound to the nucleic acids, and examine the sample for the presence of bound label; bound label indicates the presence of duplex damage or errors, while the absence of bound label, or a quantity of bound label comparable to the noise level, indicates normal duplexes.

Conditions or disorders characterized by damaged or erroneous duplexes in localized areas, such as cancers, can be treated using active sterically demanding intercalating compounds. Upon entry into a cell, the compounds intercalate at damaged or mismatched sites in the DNA. In some cases, the presence of a compound intercalated between the bases is sufficient to trigger cellular activity, up to and including apoptosis. Normal DNA is not affected. If binding is not sufficient, the cells are then exposed to sufficient illumination to photolyse the DNA where compounds are intercalated. DNA photolysis triggers various cellular mechanisms, including apoptosis, thus eliminating affected cells. The suitability of compounds of the invention for such uses can be assayed using the procedures provided in the examples below, or further by conducting photocleavage titration using transformed cell lines or clinical tumor samples instead of naked DNA oligonucleotides.

Sterically demanding intercalating compounds can be administered orally or parenterally, for example by injection, inhalation, transdermally, and the like, and can be administered in vivo or ex vivo. For example, one can use compounds of the invention to purge bone marrow of tumor cells prior to reintroducing the marrow into a patient (e.g., after radiotherapy). The compounds can be administered systemically or locally, for example via indwelling catheter, controlled- or sustained-release implant, minipump, and the like. Alternatively, the compounds can be formulated as an aerosol, and administered to the lungs and trachea.

The compounds can be formulated in a liquid dosage form such as, for example, liquids, suspensions or the like, preferably in unit dosage forms suitable for single administration of precise dosages. Liquid dosages may be administered by injection or infusion, as nose drops or as an aerosol. Alternatively, the active compound can be prepared as a creme or an ointment composition and applied topically. As another alternative, delivery may occur by controlled release of these agents by encapsulation either in bulk or at a microscopic level using synthetic polymers, such as silicone, and natural polymers such as gelatin and cellulose. The release rate can be controlled by proper choice of the polymeric system used to control the diffusion rate (Langer, R. S. and Peppas, N. A., Biomaterials (1981) 2:201). Natural polymers, such as gelatin and cellulose slowly dissolve in a matter of minutes to hours while silicone remains intact for a period of months. The compositions will include a conventional pharmaceutical carrier or excipient, and one or more of the active compound(s). In addition, the compositions may include other medicinal agents, pharmaceutical agents, carriers, adjuvants, etc.

The amount of compound administered will of course, be dependent on the subject being treated, the severity of the affliction, the manner of administration, the frequency of administration, and the judgment of the prescribing physician. Suitable concentrations can be determined by one of ordinary skill in the art, using only routine experimentation. The frequency of administration is desirably in the range of an hourly dose to a monthly dose, preferably from 8 times/day to once every other day, more preferably 1 to 3 times per day. Ointments containing one or more active compounds and optional pharmaceutical adjuvants in a carrier, such as, for example, water, saline, aqueous dextrose, glycerol, ethanol, and the like, can be prepared using a base such as, for example, petroleum jelly, lard, or lanolin.

Liquified pharmaceutical compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension.

The present invention is also directed to a kit or reagent system useful for practicing the methods described herein. Such a kit will contain a reagent combination comprising the essential elements required to conduct an assay according to the methods disclosed herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and usually including written instructions for the performance of assays. The kit of the present invention may include any configurations and compositions for performing the various assay formats described herein.

In all cases, the reagent system will comprise (1) a sterically hindered intercalating agent of the invention, and (2) additional reagents useful in carrying out the assay. The kit may optionally contain oligonucleotides or a substrate containing oligonucleotides specific for a gene, locus or polynucleotide sequence to be tested. A kit according to the present invention can additionally include ancillary chemicals such as the buffers and components of the solution in which interaction of nucleic acid duplexes with the intercalating agents of the invention take place.

The following examples are provided as a guide for those skilled in the art, and are not to be construed as limiting the invention in any way. All products are used according to manufacturer's instructions, and experiments are conducted under standard conditions, unless otherwise specified.

EXAMPLES

General considerations. The NMR studies ($^1$and $^{13}$C NMR, 2D-COSY, $^1$H and $^{13}$C NMR-HETCOR and decoupling experiments) were performed on a General Electric QE Plus 300 MHZ instrument using solvent as the internal standard. Electronic spectra were measured on a Varian Cary 2200 and a Beckmann DU 7400 UV/vis spectrophotometer. Mass spectral data were collected at the mass spectra facilities of the University of California, Riverside, Calif. (FAB and electrospray), and at the Macromolecular Resources Center of Colorado State University, Department of Biochemistry, Fort Collins, Colo. (MALDI and electrospray). CD spectra were measured on a Jasco J-500A spectropolarimeter. High-performance liquid chromatography (HPLC) was carried out with a HP 1050 system on a Rainin Microsorb-MV $C_{18}$ 100 A column (1.0 mL/min liquid phase, linear gradient over 45 min from 0.1% trifluoroacetic acid in water to 100% acetonitrile). Thin-layer chromatography was conducted on silica gel IB-F plates (J. T. Baker).

Unless otherwise specified, commercial chemicals were used as supplied. $RhCl_3.2H_2O$ was obtained from Johnson & Matthey or Aldrich, 9,10-phenanthrenequinone, (+)-KSb-tartrate, triflic acid, and Sephadex cation and anion exchange resins were from Aldrich, $[Rh(NH_3)_5 Cl]Cl_2$ was from Pfaltz+Bauer, MeCN of spectroscopic quality was from Merck, and chrysene was from Acros Chemicals. $d_8$-2,2'-Bipyridine was kindly donated by P. Belser and A. von Zelewsky, Fribourg University, Fribourg, Switzerland. 5,6-Chrysene-quinone (Greabe, V. C., and Honigsberger, F., Justus Liebigs Ann. Chem. (1900) 311:257-65) and [Rh(NH$_3$)$_6$](CF$_3$SO$_3$)$_3$ (Curtis, N. J., et al., 1983, J. Am. Chem. Soc. (1983) 105:5347-53) were prepared according to published procedures.

Figure 3:
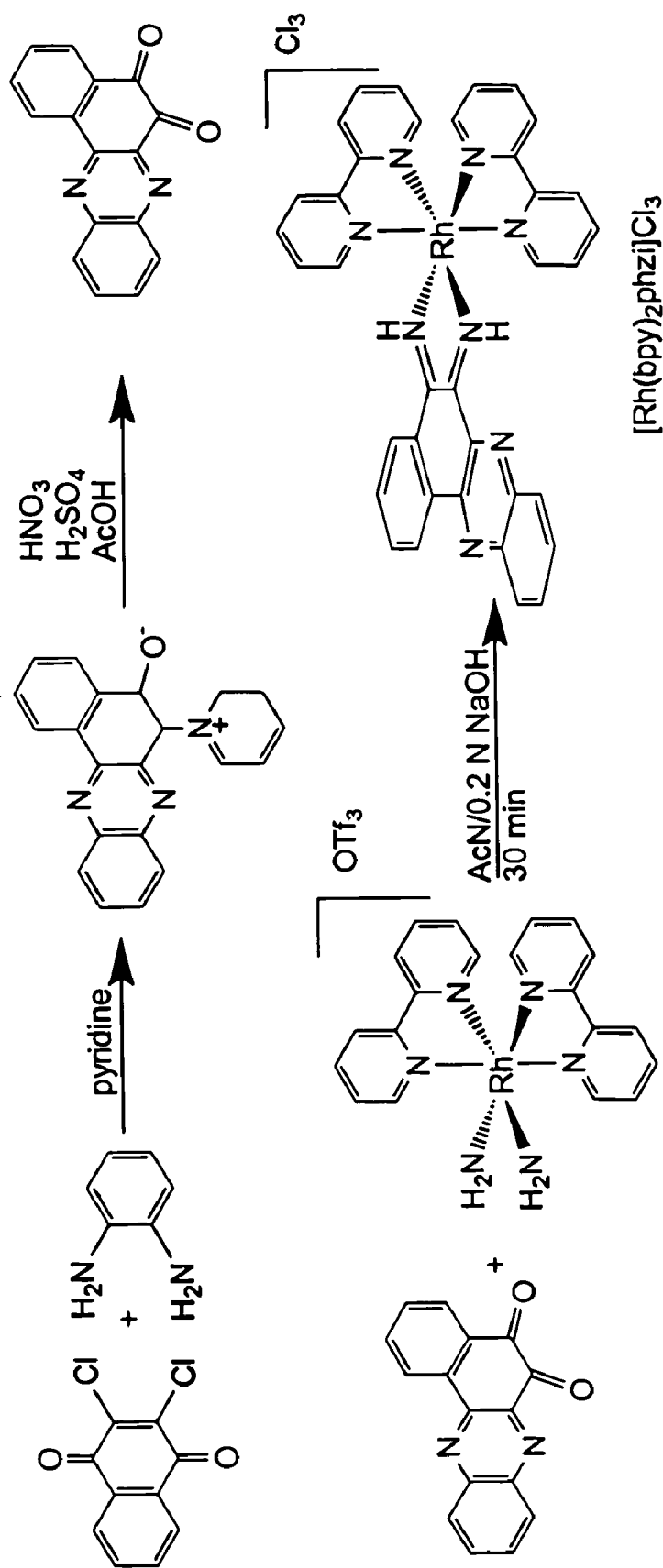
FIG. 3 depicts a reaction scheme for the synthesis of benzophenanzinequinone (phzi) and invention compound [Rh(bpy)$_2$phzi]Cl$_3$.

A reaction scheme for the synthesis of benzophenanzinequinone and [Rh(bpy)$_2$phzi]Cl$_3$ is depicted in FIG. 3.

Example 1

Synthesis of Rhodium Amine Intermediates (A) Synthesis and Characterization. rac-[Rh(phen)$_2$(NH$_3$)$_2$](PF$_6$)$_3$. Bis(amine)bis(phenanthroline)rhodium(III) was prepared as described in the literature (Gidney, P. M., et al, 1972, J. Chem. Soc., Dalton Trans. 2621-28) with the following modifications: The chloride ligands of [Rh(phen)$_2$Cl$_2$]Cl were substituted by stirring in neat triflic acid overnight (Dixon, N. E., et al., 1990, Inorg. Synth. 28:71-76). The brownish solution was carefully introduced into chilled diethyl ether. The beige precipitate was separated either by centrifugation or by filtration, dissolved in concentrated ammonia solution, and refluxed for 15-30 min. The complex was precipitated as the PF$_6$ salt, and the counterion was exchanged to chloride on a Sephadex QAE-A25 anion exchange column and finally purified on a Sephadex SP-C25 cation exchange column by elution with 0.05 M MgCl$_2$ in MeCN/water, 1:1. The fractions containing the complex were identified by TLC, combined, concentrated, and precipitated as colorless crystals by the addition of NH$_4$PF$_6$. Yield: 53%. $^1$H NMR (acetone-d$_6$ 300 MHZ): δ 9.93 (2H, d), 9.42 (2H, d), 8.99 (2H, d), 8.64 (4H, m), 8.51 (2H, d), 8.32 (2H, d), 7.87 (2H, dd), 5.18 (6H, broad s). $^{13}$C NMR (acetone-d$_6$, 75.44 MHZ): δ 154.1, 153.6, 147.6 q, 146.6 q, 142.9, 141.5, 133.2 q, 129.2, 129.1, 128.3, 127.7. MS (electrospray): 645 (35, M$^+$ −2PF$_6$), 495 (100, M$^+$ −3PF$_6$); UV/vis (MeCN/water, 1:1, 1.905×10$^{-5}$ M): 302 (12 400), 271 (51 500), 222 (51 800); R$_f$=0.45 (silica gel, MeCN/water/n-butanol/KNO$_3$, 4:1:1:0.1).

Enantiomer Separation. A 150 mg sample of the racemic mixture was separated under dark room conditions on a 150 cm long (d=3 cm) Sephadex CM-C25 ion exchange column eluting with 0.15 M (+)-potassium antimonyl tartrate in water (Keene, F. R., 1997, Coord Chem. Rev. 166:121-159). The column was washed with deionized water and then carefully blown out onto a flat surface. The resin was divided into 20 equally sized pieces and eluted individually in the dark with MeCN/water, 1:1. The fractions containing metal complex were identified by TLC. The Δ and Λ enantiomers were separated by six fractions containing no product, with the Λ enantiomer eluting faster. The Λ enantiomer fractions were reduced in volume on a rotary evaporator and then diluted to 250 mL. The Δ enantiomer fractions were brought to a total volume of 250 mL, and the concentration was determined in both cases by absorption spectroscopy. The Δε values obtained for the Λ enantiomer are approximately 15% less than for the Δ sample, revealing that heating during rotary evaporation caused partial racemization.

Δ-[Rh(phen)$_2$(NH$_3$)$_2$]Cl$_3$: CD (acetonitrile/water, 1:1, 1.93×10$^{-5}$ M): 225 (27) 266 (44), 280 (−80), 304 (−16).

Λ-: [Rh(phen)$_2$(NH$_3$)$_2$]Cl$_3$: CD (acetonitrile/water, 1:1, 2.51×10$^{-5}$ M): 227 (−19), 266 (−40), 280 (70), 303 (14).

(B) [Rh(bpy)$_2$(NH$_3$)$_2$]Cl$_3$:

The complex was synthesized according to the same procedure as described above for rac-[Rh(phen)$_2$ (NH$_3$)$_2$](PF$_6$)$_3$ with the exception that instead of precipitation as the PF$_6$ salt the compound was isolated by evaporation. Yield: 94%.

$^1$H NMR (acetone-d$_6$, 300 MHZ): δ 9.45 (2H, d), 9.05 (2H, d), 8.89 (2H, d), 8.79 (2H,) td), 8.45 (2H, td), 8.30 (2H, td), 8.05 (2H, td), 7.74 (2H, td), 5.06 (6H, broad s). MS (electrospray): 449.0 (45, M$^+$−3Cl), 447.1 (100, M$^+$ −3Cl−2H), 430.1 (45, M$^+$ −3Cl—NH$_3$); R$_f$=0.04 (silica gel, MeCN/water/n-butanol/KNO$_3$, 4:1:1:0.1).

(C) [Rh(phen)$_2$(NH$_3$)$_4$]Cl$_3$. [Rh(phen)Cl$_4$](H$_3$O$^+$) was prepared as described in the literature (McKenzie, E. D., and Plowman, R. A., 1970, J. Inorg Nucl. Chem. 32:199-212; Broomhead, J. H., and Grumley, W., 1971, Inorg. Chem. 10:2002-2009). The chloride ligands were exchanged to triflate by overnight treatment in neat triflic acid (Dixon et al. 1990, supra). The brownish solution was carefully introduced in chilled diethyl ether. The beige precipitate was separated either by centrifugation or by filtration, dissolved in concentrated ammonia solution, and refluxed for 30 min. The solution was allowed to cool and was then evaporated to dryness.

$^1$H NMR (DMSO-d$_6$, 300 MHZ): $_d$9.24 (2H, d), 9.03 (2H, d), 8.39 (2H, s), 8.27 (2H, m), 5.05 (6H, broad s), 4.04 (6H, broad s). MS (electrospray): 350.1 (32, M$^+$ 3Cl—H), 349.4 (100, M$^+$ −3Cl—2H) 348.5 (70, M$^+$ 3Cl-3H).

Example 2

Synthesis of Rhodium Intercalating Compounds (A) In a typical preparation, 50 mg of Rh(III) starting material was dissolved in 32 mL of MeCN/water, 3:1,0.1 M in NaOH. To this mixture was added 1 equiv or more of, for example, 9,10-phenanthrenequinone to produce non-hindered control DNA photocleaving compounds, or 5,6-chrysenequinone (chrysi) or benzophenanzineduimine (phzi) to produce hindered intercalating compounds. During constant stirring, the reaction was allowed to progress for approximately 18 h at room temperature. After neutralization with dilute hydrochloric acid and addition of 500 mL of water, the reaction mixture was loaded onto a Sephadex SP-C25 ion exchange column equilibrated in 0.05 M MgCl$_2$. The product was purified by elution with a gradient of 0.05-0.5 M MgCl$_2$, and the orange product bands were collected. The fractions were concentrated on a Waters Sep-Pak 5 g C$_{18}$ cartridge and washed with copious amounts of water. The metal complex was eluted from the cartridge with a minimum volume of 0.1% TFA in MeCN/water, 1:1, and lyophilized to dryness.

rac[Rh(phen)$_2$(phi)]Cl$_3$.

This orange compound was prepared according to the outline above. Yield: 86%. The characterization data are in good agreement with date in the literature (Pyle, A. M., et al. 1990, Inorg. Chem. 29:4487-4495).

Δ-[Rh(phen)$_2$(phi)](PF$_6$)$_3$.

Sodium hydroxide (0.6 g) was dissolved in 100 mL of MeCN/water, 1:1, containing

Δ-[Rh(phen)$_2$(NH$_3$)$_2$]Cl$_3$ (18.4 mg, 0.037 mmol). 9,10-Phenanthrenequinone (8 mg, 0.038 mmol) in 50 mL of acetonitrile was added and the mixture stirred at room temperature. Aliquots (400 μL) were removed at intervals and mixed with 100 μL of 1.16 M HCl in MeCN/water, 1:1. These samples were subsequently analyzed by HPLC. After 1 day, the reaction mixture was neutralized with diluted hydrochloric acid and the volume reduced to approximately 20 mL. The complex was precipitated with 1 g of NH$_4$PF$_6$ and collected on Celite. The residue was dissolved in a minimum of acetonitrile and evaporated to dryness. Yield: 26.1 mg (64%). The characterization data ($^1$H NMR, MS, CD, UV/vis) agree well with published data (Pyle, A. M., et al. 1990, J. Am. Chem. Soc. 112:9432-9434) with slightly higher Δε values observed by CD spectroscopy.

CE (acetonitrile, 1.47×10$^{-5}$ M):261 (99), 275 (−179), 346 (−24).

rac-[Rh(bpy)$_2$(phi)](PF$_6$)$_3$.

This product was synthesized starting from [Rh(bpy)$_2$(NH$_3$)$_2$]$^{3+}$. The characterization data agree well with published data (Sitlani, A., and Barton, J. K., 1994, *Biochemistry* 33:12100-12108).

rac-[Rh(bpy)$_2$(chrysi)]Cl$_3$.

[Rh(bpy)$_2$(NH$_3$)$_2$](PF$_6$)$_3$ (195.5 mg, 0.22 mmol) and 5,6-chrysenequinone (56.8 mg, 0.22 mmol) were dissolved with rapid stirring in 15 mL of acetonitrile under atmospheric conditions. Aqueous sodium hydroxide (5 mL, 0.4 M) was added and the reaction vessel capped to prevent evaporation. After 3 h the reaction was stopped by the addition of 5-6 mL of 0.4 M hydrochloric acid. The mixture was diluted, purified, and isolated as described above. Yield: 28 mg (83%).

$^1$H NMR (MeOH-d$_4$, 500 MHZ): δ 8.94 (2H, t), 8.86 (2H, t), 8.80 (1H d), 8.77 (1H, d), 8.56 (2H, split t), 8.44 (5H, m), 8.40 (1H, d), 8.15 (1H, m), 8.03 (1H, m), 7.95 (3H, m), 7.86 (1H, d), 7.81 (1H, d), 7.64 (5H, m). $^{13}$C NMR (MeOH-d$_4$, 125.73 MHZ): δ 183.3, 177.3, 175.4, 157.4, 157.2, 157.2, 153.8, 153.2, 152.1, 144.6, 144.5, 143.9, 143.8, 139.7, 138.8, 138.4, 136.2, 135.7, 132.3, 132.2, 132.0, 131.8, 130.9, 130.77, 130.6, 130.2, 129.4, 127.7, 127.6, 127.3, 126.9, 126.8, 123.9, 122.9, 120.8, 118.6, 116.3, 114.1. MS (FAB): 671 (24% M$^+$ −3Cl), 670.1 (63, M$^+$ −3Cl—H), 669.1 (100, M$^+$ −3Cl-2H); UV/vis (water, 7.76×10$^{-6}$ M): 303 (57 000), 315 (52 200), 391 (10 600). $\epsilon_{271\ nm}$:63 800 M$^{-1}$ cm$^{-1}$ (pH isosbestic point); R$_f$=0.33 (silica gel, MeCN/water/n-butanol/KNO$_3$, 4:1:1:0.1).

(B) Enantiomeric Separation.

The enantiomers of the complex were separated on a Sephadex SP-C25 column eluted with 0.15 M of (+)-KSb tartrate in water (Keene, 1997, supra) The separated orange fractions, with the Λ enantiomer being eluted faster, were collected and concentrated on a Waters Sep-Pak 5 g C$_{18}$ cartridge. After washing with water, the residue was dissolved in a minimum of MeCN/water, 1:1, and evaporated to dryness.

Δ-[Rh(bpy)$_2$(chrysi)]Cl$_3$: CD (water, 7.76×10$^{-6}$ M): 233 (34) 264 (26), 286 (−12), 308 (−42), 318 (−100), 341 (6).

Λ-[Rh(bpy)$_2$(chrysi)]Cl$_3$: CD (water, 7.76×10$^{-6}$ M): 233 (−34) 264 (−26), 286 (12), 308 (42), 318 (100), 341 (−6).

rac-[Rh(d$_8$-bpy)$_2$(chrysi)]Cl$_3$: This complex was synthesized as above but with deuterated 2,2'-bipyridine.

rac-[Rh(phen)$_2$(chrysi)]Cl$_3$: This compound was prepared analogously to rac-[Rh(bpy)$_2$(chrysi)]Cl$_3$. Yield: 77%.

rac-[Rh(phen)(phi)$_2$]Cl$_3$: This orange compound was prepared from

[Rh(phen)(NH$_3$)$_4$]Cl$_3$ with 2 equiv of 9,10-phenanthrenequinone following the outline above. The product was purified on a Sephadex SP-C25 cation exchange column eluting with 1.0 M MgCl$_2$ acidified with a few drops of diluted HCl. Yield: 54%. The characterization data are in good agreement with the literature (Sitlani, 1994, supra).

rac-[Rb(phen)(chrysi)$_2$]Cl$_3$: This orange/brown compound was prepared from [Rh(phen)(NH$_3$)$_4$]Cl$_3$ with 5 eq of chrysene quinone as described above, and purified using the method described for [Rh(phen)(phi)$_2$]Cl$_3$. Yield: 48%.

rac-[Rh(phen)(phi)(chrysi)]Cl$_3$: [Rh(phen)(NH$_3$)$_4$](CF$_3$SO$_3$)$_3$ (17 mg, 0.021 mmol) was combined with 9,10-phenanthrenequinone (5.4 mg, 0.026 mmol) in acetonitrile (9.6 mL), water (2.0 mL), and NaOH solution (1.6 M, 1.2 mL). After 60 min of stirring at ambient temperature, 5,6-chrysenequinone (9.9 mg, 0.039 mmol) was added. The reaction was stopped after 20 h by neutralization with diluted hydrochloric acid. The product was purified on a Sephadex SP-C25 cation exchange column eluting with a gradient of 0.05-0.5 M MgCl$_2$. The red product band was collected, and the fractions were concentrated on a Waters Sep-Pak, 5 g C$_{18}$ cartridge and washed with copious amounts of water. The metal complex was eluted from the cartridge with a minimum volume of 0.1% TFA in MeCN/water, 1:1, and lyophilized to dryness. Yield: 14 mg (75%). $^1$H NMR (D$_2$O, 300 MHZ): complicated multiplets centered at 8.94, 8.36, 8.08, 7.80, and 7.60. Integrals were consistent with the desired product.

MS (electrospray): 745.3 (18, M$^+$ −3Cl), 744.3 (75, M$^+$ −3Cl-1H), 743.2 (100, M$^+$ −3Cl-2H).

Example 3

Photocleavage

A set of DNA duplexes was prepared having the following sequence: 3'-GTGTACGTXCTGAGGCG-5' (SEQ ID NO:1)

5'-CACATGCAYGACTCCGC-3' (SEQ ID NO:2), where X and Y were varied to provide A-T, G-C, and the following mismatches: C-C, C-A, T-T, A-A, T-C, T-G, G-A, and G-G. All oligonucleotides were prepared using standard phosphoramidite chemistry, and were purified by reverse phase HPLC. The oligonucleotides were 5' end-labeled with γ-$^{32}$P ATP (Dupont-NEN) and T4 polynucleotide kinase (New England Biolabs).

Duplexes (10 μM) were incubated with Δ or Λ [Rh(bpy)2(chrysi)]$^{3+}$ (1 μM in 50 mM Tris, 20 mM NaOAc, 18 mM NaCl, pH 7.0) for 11 minutes, then irradiated for 13 min at 365 nm using an Oriel HgXe arc lamp. The products were analyzed by PAGE (20%, denaturing), imaged using a Molecular Dynamics Phosphorimager. The strongest cleavage intensity was observed with the Δ enantiomer on the duplex containing the C-C mismatch. Here, cleavage occurred to the 3' side of the mismatch site. Similar, although less intense cleavage was observed at the other pyrimidine-pyrimidine mismatches T-T and T-C. C-A, the single purine-pyrimidine mismatch that is cleaved, showed a different pattern. Strong cutting is evident at the mismatched C and neighboring the base 3' to the mismatch site. Unlike the other recognized mismatches, the cleavage 3' to C-A results in two products having different gel mobility, possibly the result of chemically different polymer termini. The cleavage of A-A was also distinctive. The Δ enantiomer promotes strong cleavage at the base 3' to the site, and a small amount of cleavage at the A-A site itself. The A-A mismatch is the only pair cleaved by the Λ enantiomer, with weaker cleavage than the Δ enantiomer.

Other DNA photocleavage experiments on similar systems showed DNA cleavage by Δ-[Rh(bpy)$_2$(chrysi)]$^{3+}$ is affected by the bases to the 5' and 3' side of the mismatch site (T/A in SEQ ID NO:1 and C/G in SEQ ID NO:4). When these bases were systematically changed, photocleavage was observed at 83 of 104 of the mismatch-sequence context combinations (80%).

Example 4

Photocleavage Titration

A hairpin DNA oligonucleotide was synthesized with the sequence:
5'-CATCATGTCCTGCCCTTTTTGGGCACGA-CATGATG-3' (SEQ ID NO:3), having a single C-C mismatch. The hairpin was photocleaved as described in Example 2 above with Δ-[Rh(bpy)$_2$ (chrysi)]$^{3+}$ at either 313 nm or 365 nm for 7.5 to 15 min. Hairpin DNA concentration was varied from $3\times10^{-10}$ M to $1\times10^{-4}$ M, with the Rh complex used at 0.10× the DNA concentration. The cleavage products were eluted through 20% denaturing polyacrylamide gels, and analyzed using a Molecular Dynamics Phosphorimager and ImageQuant software. Cleavage was observed 3' to the C-C mismatch on both sides of the hairpin: only the cleavage band closest to the end label was quantitated. Data from multiple trials was normalized (open circles) and fit to a standard single binding site binding model (solid line).

The thermodynamic binding constant was determined to be $8.4 (.+-.1.0)\times10^5$ M$^{-1}$. Similar DNA photocleavage titrations at other mismatch sites have measured the affinity of Δ-[Rh(bpy)$_2$(chrysi)]$^{3+}$ between $1\times10^7$ and $3\times10^5$ M$^{-1}$. To examine the level of selectivity, the average binding constant of Δ-[Rh(bpy)$_2$(chrysi)]$^{3+}$ to B-form DNA was also determined. Photocleavage on a 33 mer correctly matched hairpin and competitive titration with unlabeled 25mer B-DNA yielded a value of $4 (.+-.2)\times10^4$ M$^{-1}$ for the average non-specific binding Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the claims.

What is claimed is:

1. A compound, comprising a cationic moiety of the formula:

$$M(R_1)(R_2)(R_3)^{3+}$$

wherein:

M is a metal selected from a group consisting of Rh, Ru, Co, Fe, Cr, Cu, Zn, Cd, and Pb, each of $R_1$ and $R_2$ is a ligand independently selected from a group consisting of ethylenediamine or a substituted derivative thereof, and an aryl or heteroaryl comprising 1 to 5 rings; and $R_3$ is a ligand having the following structure:

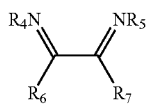

wherein:

each of $R_4$ and $R_5$ is independently selected from a group consisting of —H and a lower alkyl, $R_6$ and $R_7$ are taken together to form a substituted or an unsubstituted fused heteroaryl ring system comprising at least four rings, wherein each ring contains from 0 to 2 heteroatoms, and wherein the substituents in the substituted ring system are selected from a group consisting of —H, —R, halo, —OH, —OR, —NH$_2$, —NHR, —NR$_2$, —CN, —NO$_2$, —SH, —SO$_3$, —OSO$_3$, —C(O)OH, —C(O)OR, —C(O)NH$_2$, —C(O)NHR, —C(O)NR$_2$, —SO$_3$R, and —OSO$_3$R, wherein each R is independently selected from a group consisting of a lower alkyl, a cycloalkyl, a lower alkenyl, a lower alkynyl, and phenyl, with the further proviso that in the fused heteroaryl ring system, at least one ring contains 1 or 2 heteroatoms.

2. The compound according to claim 1, wherein the heteroatoms are independently selected from a group consisting of nitrogen, oxygen, or sulfur.

3. The compound according to claim 2, wherein each of the heteroatoms is nitrogen.

4. The compound according to claim 3, wherein $R_3$ is:

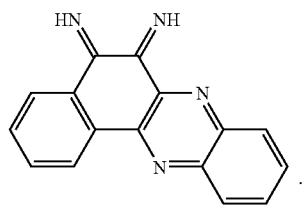

5. The compound according to claim 3, wherein $R_3$ is:

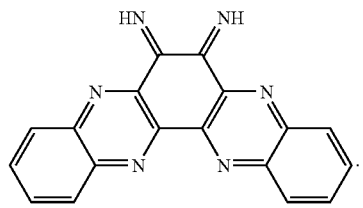

6. The compound according to claim 1, wherein M is Rh.

7. The compound according to claim 1, wherein each of $R_1$ and $R_2$ is independently selected from a group consisting of 2,2'-bipyridine, 4,4'-dimethyl-2,2'-bipyridine, and 4,4'-diamido-2,2'-bipyridine.

8. The compound according to claim 1, wherein each of $R_1$ and $R_2$ comprises a 5-phenanthrolyl substituent.

9. The compound according to claim 1, wherein each of $R_4$ and $R_5$ is —H.

10. The compound according to claim 1, wherein:
M is selected from a group consisting of Rh and Ru;
each of $R_1$ and $R_2$ is 2,2'-bipyridine; and
$R_3$ is:

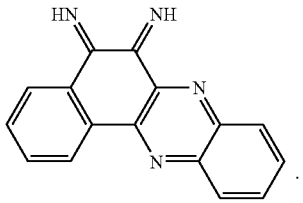

11. A compound, comprising a cationic moiety of the formula:

wherein:
M is a metal selected from a group consisting of Rh, Ru, Co, Fe, Cr, Cu, Zn, Cd, and Pb;
each of $R_1$ and $R_2$ is a ligand independently selected from a group consisting of ethylenediamine and an aryl or heteroaryl comprising between 1 and 5 rings, and
$R_3$ is a ligand having the following structure:

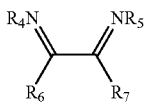

wherein:
each of $R_4$ and $R_5$ is independently selected from a group consisting of —H and a lower alkyl;
$R_6$ and $R_7$ are taken together to form a substituted or an unsubstituted fused heteroaryl ring system comprising at least four rings, wherein each ring contains from 0 to 2 heteroatoms, and wherein the substituents in the substituted ring system are selected from a group consisting of —H, —R, halo, —OH, —OR, —NH$_2$, —NHR, —NR$_2$, —CN, —NO$_2$, —SH, —SO$_3$, —OSO$_3$, —C(O)OH, —C(O)OR, —C(O)NH$_2$, —C(O)NHR, —C(O)NR$_2$, —SO$_3$R, and —OSO$_3$R, wherein each R is independently selected from a group consisting of a lower alkyl, a cycloalkyl, a lower alkenyl, a lower alkynyl, and phenyl,
with the further proviso that in the fused heteroaryl ring system, at least one ring contains 1 or 2 heteroatoms.

12. The compound according to claim 11, wherein the heteroatoms are independently selected from a group consisting of nitrogen, oxygen, or sulfur.

13. The compound according to claim 12, wherein each of the heteroatoms is nitrogen.

14. The compound according to claim 13, wherein $R_3$ is:

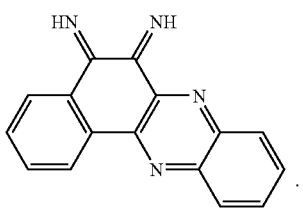

15. The compound according to claim 13, wherein $R_3$ is:

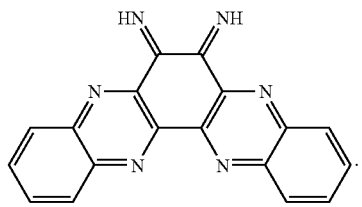

16. The compound according to claim 11, wherein M is Rh.

17. The compound according to claim 11, wherein each of $R_1$ and $R_2$ is independently selected from a group consisting of 2,2'-bipyridine, 4,4'-dimethyl-2,2'-bipyridine, and 4,4'-diamido-2,2'-bipyridine.

18. The compound according to claim 11, wherein each of $R_1$ and $R_2$ comprises a 5-phenanthrolyl substituent.

19. The compound according to claim 11, wherein each of $R_4$ and $R_5$ is —H.

20. The compound according to claim 11, wherein:
M is selected from a group consisting of Rh and Ru;
each of $R_1$ and $R_2$ is 2,2'-bipyridine; and
$R_3$ is:

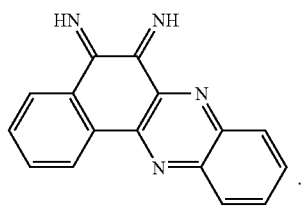

21. The compound according to claim 20, wherein M is Rh.

22. The compound according to any one of claims 1, 2-5, or 6-21, wherein the compound is a neutral salt.

23. The compound according to claim 22, wherein the salt is a chloride salt.

24. A compound, comprising a chloride salt of a cation of the formula:

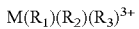

wherein:
M is a metal selected from a group consisting of Rh, Ru, Co, Fe, Cr, Cu, Zn, Cd, and Pb;
each of $R_1$ and $R_2$ is a ligand independently selected from a group consisting of ethylenediamine and an aryl or heteroaryl comprising between 1 and 5 rings, and
$R_3$ is a ligand having the structure:

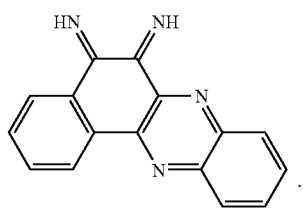

25. A compound, comprising a chloride salt of a cation of the formula:
$$M(R_1)(R_2)(R_3)^{3+}$$
wherein:
M is a metal selected from a group consisting of Rh, Ru, Co, Fe, Cr, Cu, Zn, Cd, and Pb;
each of $R_1$ and $R_2$ is a ligand independently selected from a group consisting of ethylenediamine and an aryl or heteroaryl comprising between 1 and 5 rings, and
$R_3$ is a ligand having the structure:
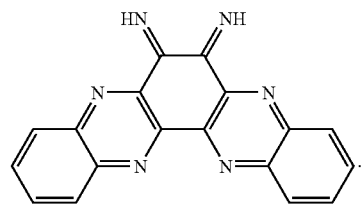
.
* * * * *

SEQUENCE LISTING

```
<160> NUMBER OF SEQ ID NOS: 6

<210> SEQ ID NO 1
<211> LENGTH: 17
<212> TYPE: DNA
<213> ORGANISM: Artificial sequence
<220> FEATURE:
<223> OTHER INFORMATION: String of DNA duplex
<220> FEATURE:
<221> NAME/KEY: misc_feature
<222> LOCATION: (9)..(9)
<223> OTHER INFORMATION: n is any nucleotide

<400> SEQUENCE: 1
gcggagtcnt gcatgtg                                                    17

<210> SEQ ID NO 2
<211> LENGTH: 17
<212> TYPE: DNA
<213> ORGANISM: Artificial sequence
<220> FEATURE:
<223> OTHER INFORMATION: String of DNA duplex
<220> FEATURE:
<221> NAME/KEY: misc_feature
<222> LOCATION: (9)..(9)
<223> OTHER INFORMATION: n is any nucleotide

<400> SEQUENCE: 2
cacatgcang actccgc                                                    17

<210> SEQ ID NO 3
<211> LENGTH: 35
<212> TYPE: DNA
<213> ORGANISM: Artificial sequence
<220> FEATURE:
<223> OTHER INFORMATION: Hairpin DNA oligonucleotide

<400> SEQUENCE: 3
catcatgtcc tgccctttt gggcacgaca tgatg                                 35

<210> SEQ ID NO 4
<211> LENGTH: 17
<212> TYPE: DNA
<213> ORGANISM: Artificial sequence
<220> FEATURE:
<223> OTHER INFORMATION: String of DNA duplex
<220> FEATURE:
<221> NAME/KEY: misc_feature
<222> LOCATION: (9)..(9)
<223> OTHER INFORMATION: n is any nucleotide
```

```
-continued

<400> SEQUENCE: 4
gcggagtcnc gcatgtg                                                         17

<210> SEQ ID NO 5
<211> LENGTH: 31
<212> TYPE: DNA
<213> ORGANISM: Artificial sequence
<220> FEATURE:
<223> OTHER INFORMATION: String of DNA duplex

<400> SEQUENCE: 5
gatgtcggtc ccacgatggt gacggattac c                                         31

<210> SEQ ID NO 6
<211> LENGTH: 41
<212> TYPE: DNA
<213> ORGANISM: Artificial sequence
<220> FEATURE:
<223> OTHER INFORMATION: String of DNA duplex

<400> SEQUENCE: 6
gagttggtaa tccgtcacca tcgtgcgacc gacatcatgc g                              41
```